(12) United States Patent
Su et al.

(10) Patent No.: US 7,621,638 B2
(45) Date of Patent: Nov. 24, 2009

(54) DELIVERING A SHORT ARC LAMP LIGHT FOR EYE IMAGING

(75) Inventors: Wei Su, Sunnyvale, CA (US); Yan Zhou, Pleasanton, CA (US); Yeou-Yen Cheng, Saratoga, CA (US); Qing Chun Zhao, Sunnyvale, CA (US)

(73) Assignee: Clarity Medical Systems, Inc., Pleasanton, CA (US)

( * ) Notice: Subject to any disclaimer, the term of this patent is extended or adjusted under 35 U.S.C. 154(b) by 183 days.

(21) Appl. No.: 11/606,597

(22) Filed: Nov. 29, 2006

(65) Prior Publication Data

US 2008/0123052 A1    May 29, 2008

(51) Int. Cl.
*A61B 3/10* (2006.01)
*F21V 7/00* (2006.01)

(52) U.S. Cl. .................. 351/221; 362/300; 362/302
(58) Field of Classification Search ............... 351/200, 351/205, 206, 221; 362/296–298, 300, 302, 362/304, 305, 307
See application file for complete search history.

(56) References Cited

U.S. PATENT DOCUMENTS

| | | | |
|---|---|---|---|
| 4,275,335 A | 6/1981 | Ishida | |
| 5,098,184 A | 3/1992 | van den Brandt et al. | |
| 5,418,583 A | 5/1995 | Masumoto | |
| 5,608,472 A | 3/1997 | Szirth et al. | |
| 5,822,036 A | 10/1998 | Massie et al. | |
| 6,361,167 B1 | 3/2002 | Su et al. | |
| 6,603,134 B1 * | 8/2003 | Wild et al. | 250/526 |
| 6,685,317 B2 | 2/2004 | Su et al. | |
| 6,729,727 B2 * | 5/2004 | Nanjo | 351/206 |
| 6,921,169 B2 | 7/2005 | Su et al. | |
| 6,986,591 B2 * | 1/2006 | Pate | 362/296 |
| 7,241,014 B2 * | 7/2007 | Lippey et al. | 353/8 |
| 2002/0122621 A1 * | 9/2002 | Li | 385/31 |
| 2003/0198456 A1 * | 10/2003 | Steiner et al. | 385/146 |
| 2007/0123761 A1 * | 5/2007 | Daly et al. | 600/316 |
| 2007/0272669 A1 * | 11/2007 | Comley et al. | 219/121.76 |

* cited by examiner

*Primary Examiner*—Huy K Mai
(74) *Attorney, Agent, or Firm*—Charles E. Krueger

(57) ABSTRACT

A light delivery technique includes optical configurations as well as the associated methods that generate a ring beam from a linear light source. In one embodiment, a remote light source module delivers illumination light to a fundus camera and/or slit lamp. In another embodiment, an arrangement combines the use of a light pipe homogenizer and a ring beam transformer for efficiently collecting light from a substantially axially linear light source, homogenizing the collected light that lacks low angle flux relative to the optical axis, and transforming the light into a ring beam with a substantially improved low angle flux distribution. In still another embodiment, light emitted from a substantially axially linear light source is directly collected by a curved surface mirror and spatially filtered into a ring beam. The ring illumination beam can be co-axially projected on a sample such as the pupil of a human eye and at the same time the light beam also has a large enough relatively uniform angular flux distribution so that a wide area on the retina of the eye can be uniformly illuminated.

16 Claims, 7 Drawing Sheets

DELIVERING A SHORT ARC LAMP LIGHT FOR EYE IMAGING

BACKGROUND OF THE INVENTION

Arc lamps have been used in many applications, including camera strobes, analytical instrumentation, surgical illumination, theatrical lighting, and laser and machine vision. In spite of the availability of other more convenient and low cost light sources such as LEDs (light emitting diodes), Arc lamps are still currently used in some niche areas because they have certain unique properties that other light sources cannot provide. These include high brightness, high power, high UV (ultra violet) light content, a wide continuous spectral distribution with excellent color balance and spectral flatness in the visible region, long life, and stable spectrum over life.

Arc lamps have two operation modes, namely DC and pulsed mode. The DC operation mode generally has a better arc stability and substantially longer life. However, this mode of operation is not ideal for photography, which only needs a short flash of illumination light while a photo is being taken. As for the pulsed mode of operation, the combination of wide spectrum and color balance with the ability to produce short pulses of high brightness light has made Arc lamps particularly suitable for biological photography, enabling excellent color projection and high-quality flesh tones. In this respect, short-arc flash lamps with an arc spacing of typically 1-3 mm are especially unique because they can provide pulses of high intensity and brightness light that other light sources cannot match. The high brightness and intensity is particularly desirable for superior camera performance. In addition, a short-arc flash lamp can also solve the problem of motion of a living biological sample such as a human eye and hence eliminate blurring of the obtained image. Furthermore, the wide spectral distribution of Arc flash lamps also makes them ideal for applications requiring light in specific spectral regions, such as red-free images and Fluorescein Angiography. The specific spectral region can be selected by placing different types of optical filter in the illumination and/or detection light path.

In spite of its wide use in biological imaging applications, the structure of an Arc lamp makes it difficult to efficiently collect the emitted light and deliver it to the object to be imaged with excellent uniformity. In general, the discharge formed between the two Arc lamp electrodes is a wandering but relatively linear light source. An ellipsoidal reflector can be used for relatively high efficiency light collection, and in such a case the lamp is usually aligned along the optical axis, with the arc at the first focus. A fiber optic bundle is usually placed with its input end at the second focus to collect the light. Although this arrangement focuses a relatively large portion of the available light from the arc, since the electrode will obstruct the light at angles of less than about 30 degrees from the optical axis, there is little light converging into the fiber bundle at angles close to the optical axis. This will cause problems in terms of light illumination uniformity for eye fundus imaging.

On the other side of the fiber optic bundle, the fiber bundle emitted light needs to be projected uniformly onto the object. Traditionally, this is done by some combination of conventional condensing lenses and/or spherical mirrors. For digital eye fundus imaging or photography, such a projection arrangement is not ideal. Commonly assigned U.S. Pat. No. 6,921,169 discloses an eye camera for imaging the retina. As pointed out in that patent, it is desirable to have a ring illumination beam to be co-axially projected on the eye lens so that illumination light is not reflected from the cornea, lens, and other parts of the eye to cause flair in the image. Further, the light beam must have a uniform as well as a wide enough angular distribution such that when the illumination beam is projected onto the retina of the eye, not only the central area of retina will be illuminated, but also the peripheral area of the retina can be substantially illuminated. However, existing ring beam projection schemes failed to achieve this in a cost effective way.

In a traditional ophthalmic instrument such as a photographic fundus camera, the illumination source is generally a combination light source module consisting of a continuous light source, typically a Halogen lamp, and a flash lamp, which is generally an Arc lamp. Either a removable beam splitter/mirror is used to combine the two light beams, or the filament of the continuous light source is imaged onto the gap between the two electrodes of the flash lamp to make them appear as one. The continuous light source provides aiming illumination for the photographer/imager, while the flash light source provides high energy pulse needed for high quality photography. The same type of configuration is widely used in both photographic fundus cameras for the posterior and slit lamp cameras for the anterior chamber of the eye. Such a module is complicated and expensive as it needs to combine two different light sources.

TECHNICAL FIELD

The present disclosure relates generally to an optical apparatus and methods for ophthalmic applications. In particular, it is related to an optical arrangement for collecting light from an axially linear light source, delivering it to an ophthalmic instrument for general illumination, and transforming the delivered light into a ring beam for retina imaging.

DESCRIPTION OF EXAMPLE EMBODIMENTS

Overview

Novel embodiments of optical configurations and methods are described for collecting and conditioning light from a single remotely located axially linear light source that can supply both continuous and pulse illumination. The conditioned light is transmitted through an optical fiber bundle and/or used directly as the light source for observing and imaging the anterior/posterior chamber of the eye in an optical system. In one embodiment, before being projected into the eye, the light beam is manipulated and spatially filtered, and eventually transformed into a light beam of ring shape. The ring illumination beam can then be co-axially projected onto the posterior part of a human eye and the light beam has a sufficiently large relatively uniform angular flux distribution so that a wide area on the retina of the eye can also be uniformly illuminated.

In another embodiment, a light homogenizer is combined with a ring beam transformer for a remotely located arc lamp. The light homogenizer improves the spatial and angular uniformity for a light beam collected from an arc lamp. The ring beam transformer efficiently converts optical radiation from a linear light source into a light beam of ring shape. Another embodiment is the direct collection of light from a linear light source using a curved surface mirror and spatially filtering the light beam into a desired ring beam having a desired numerical aperture.

Description

Reference will now be made in detail to various embodiments of the invention. Examples of these embodiments are illustrated in the accompanying drawings. While the invention will be described in conjunction with these embodiments, it will be understood that it is not intended to limit the invention to any embodiment. On the contrary, it is intended to cover alternatives, modifications, and equivalents as may be included within the spirit and scope of the invention as defined by the appended claims. In the following description, numerous specific details are set forth in order to provide a thorough understanding of the various embodiments. However, the present invention may be practiced without some or all of these specific details. In other instances, well known process operations have not been described in detail in order not to unnecessarily obscure the present invention.

Figure 1:
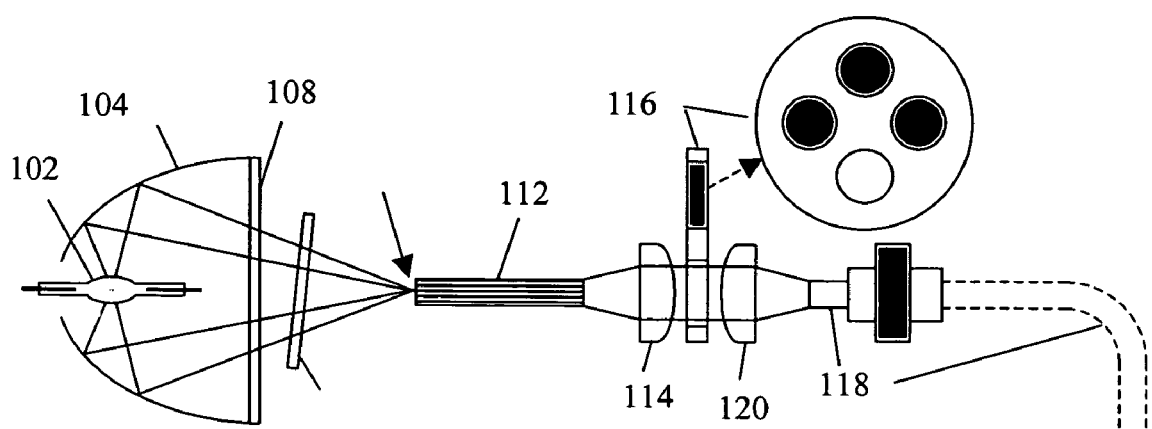
FIG. 1 shows an embodiment of a light collection and homogenization configuration.
Figure 2:
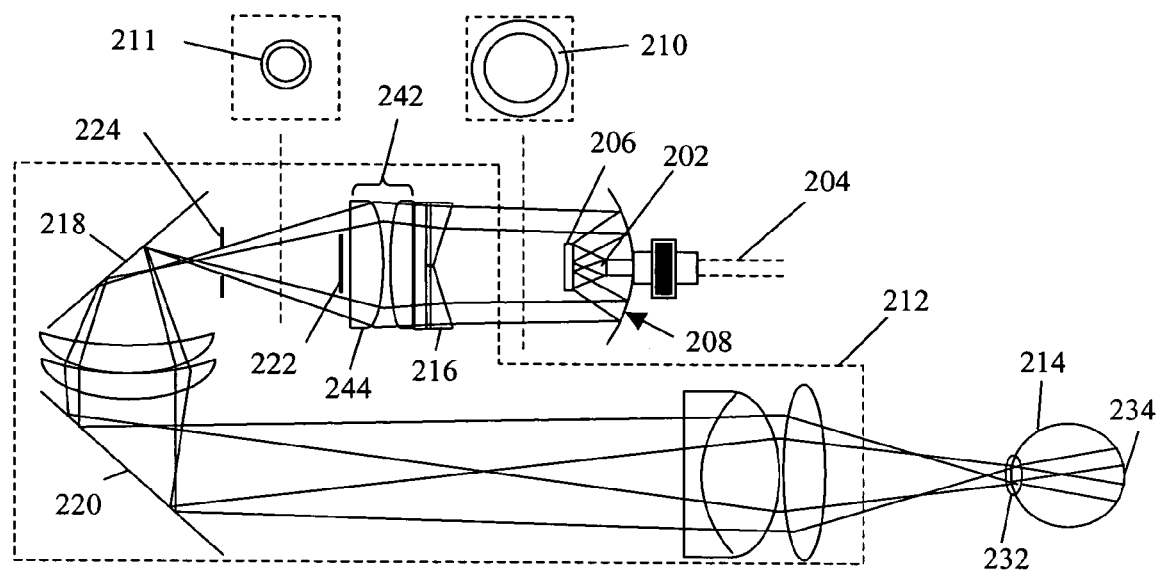
FIG. 2 shows an example of the use of a solid optically transparent cone as the ring beam transformer.

FIGS. 1 and 2 show one embodiment. In this embodiment a light source module depicted in FIG. 1 can be remote from the ophthalmic system optics that are depicted in FIG. 2. The light is coupled from the light source module to the ophthalmic system by a fiber optic bundle. The distribution of components depicted in the embodiment of FIGS. 1 and 2 is presented by way of example, not limitation. For example, filters may be located in either the light source module or the ophthalmic system. The use of a remote light source allows the ophthalmic system to be lighter and more compact. In other situations, it could be desirable to integrate the light source into the ophthalmic system.

A relatively large amount of light from an axially linear light source of an Arc flash tube 102 is reflected by an ellipsoidal mirror 104 and directed to the second focal point 106 of the ellipsoidal mirror 104. A safety plate 108 which, for example, can be a piece of quartz, having a high optical transparency in, at least, the visible spectral range can be arranged next to the ellipsoidal mirror 104. Although this safety plate is not absolutely required, in case of an explosion or breaking of the Arc lamp tube, this safety plate can prevent the shattering pieces from damaging other parts of the Arc flash lamp module. A UV (ultraviolet) and IR (infrared) filter 110, which may comprise a single or a multiple number of filters that will prevent the transmission of UV and IR light but will only transmit the visible part of the Arc lamp spectrum, is preferably arranged in the optical path. This UV and IR filter 110 is also preferably tilted with its normal at a certain angle with respect to the optical axis so that the reflected UV and IR radiation will not be directed back to the Arc flash tube 102 to increase the temperature of the tube.

Instead of directly placing the input end of a fiber optic bundle at the second focus 106 of the ellipsoidal mirror 104, a light pipe homogenizer 112 is used to collect and homogenize the light from the Arc lamp tube 102. The input end of the light pipe homogenizer 112 is preferably placed substantially at the second focus location 106 of the ellipsoidal mirror, and as a result, a relatively large portion of light from the Arc flash tube 102 will be collected by the light pipe homogenizer 112. As mentioned in the background section of the application, the electrode of the Arc flash tube 102 will block a certain portion of light with emission angles within about 30 degrees relative to the optical axis and prevent this portion of light from entering the light pipe homogenizer 112, therefore causing non-uniform angular distribution of radiation at the focus point. The light homogenizer 112 enables those light rays that entered the light pipe homogenizer 112 to bounce off the walls multiple times. At the other end of the light pipe homogenizer 112, the spatial and angular distribution of the radiation flux of the emerging light is improved substantially.

The light beam emitted from the light pipe homogenizer 112 can be substantially collimated by a lens 114. A filter wheel 116 can be placed behind the lens 114 so that the spectrum of the illumination light beam can be further selected by positioning the appropriate filter mounted on the filter wheel 116 into the light path. Note that in addition to color filters, band pass and/or long/short pass filters, the filter can be of any spectral selection type such as a multiple band pass filter and can also be a neutral density filter to simply attenuate the light or an open hole to simply pass the light beam without attenuation. A benefit of using a neutral density filter to attenuate the optical power instead of directly reducing the discharge current or voltage sent to the Arc lamp tube 102 is that the stability of the light output will be much better than in the case of directly driving the Arc lamp tube 102 at a lower power level. This is especially true for the DC operation mode of the Arc lamp. A fiber optic bundle 118 can be arranged at the focal plane of a second lens 120 to collect the conditioned light. The homogenizing effect of the light pipe reduces the intensity of hot spot from the lamp projected onto the end of the fiber bundle and extends the lifetime of the fiber bundle. The illumination light source module represented by FIG. 1 can be considered as an independent external standalone item remote from an ophthalmic instrument, such as a fundus camera or a slit lamp, or part of a combination system that requires an arc flash light for both pulse and continuous modes of illumination. Such an arrangement will be very suitable for easy replacement in the field.

The light emerging from the other end of the fiber bundle 118 exhibits uniform distribution in spatial and angular fashion. The fiber bundle could be used as a uniform area light source having various cross-sectional shapes. In the present embodiment, the fiber bundle is also used as an illumination light source in a slit light projection system for imaging the anterior chamber of the eye.

In another embodiment, a fiber bundle with a circular cross section at both ends of the bundle is used. As shown in FIG. 2, a solid optical device with the shape of a cone 202 is used to transform the light source from a circular disk of a fiber bundle to an axially linear light source. The optically transparent device 202 is preferably bonded to the output end of the fiber optic bundle 204 with optically clear glue for better light coupling. A small mirror 206 is used to redirect the light from the cone 202 to a reflector 208 so that the fiber bundle could be inserted into the optical path from a small opening at the center of the reflector 208. The result is a more compact design and less obstruction to the light beam.

The function of the catadioptric optical system, consisting of parabaloidal mirror 208, axicon lens 216 and condensing lens group 242, is to convert the equivalent linear light source into a light beam with hollow ring shape. The term "ring beam transformer" is used to describe its general function. The axially linear light source or its equivalent is located near the focal point of the parabaloidal mirror 208. The emerging light beam from the mirror 208 is nearly collimated with a small dark hole along the optical axis due to the obstruction from the mirror 206. The refractive effect of the axicon lens 216 changes the direction of the collimated beam radially in the fashion that the tilted beam is symmetric along the optical axis. The condensing lens group 242 further forms the ring light beam at the back focal plane of the second condensing lens 244 of the group 242, with right converging angles. This radial-outwardly-deflected ring beam can then be relayed and/or imaged onto the eye lens of the patient using various optical beam manipulation and/or relay configurations. The size and width of the ring light beam could be adjusted by changing the focal length of the condensing lenses and/or angle of the two optical surfaces of the axicon lens 216.

The ring beam, when focused onto the anterior portion 232 of the eye, will have a narrow annular ring width, and hence can be aligned to be slightly within the iris but outside the imaging path of the fundus camera such that there is no overlap of the illumination beam with the imaging beam to cause any flair appearing in the retina image as a result of illumination light scattering by the cornea, the iris or the crystal lens, as is well known to those skilled in the art. On the retina 234, due to the fact that the illumination beam has a certain numerical aperture with a homogenized uniform angular distribution of the optical intensity, the beam will spread out evenly to cover a large portion of the retina 234. On the other hand, if the illumination beam were not homogenized, a non-uniform angular distribution of the optical intensity would cause certain regions on the retina that correspond to the darker angular range of the beam to appear less illuminated.

At the expense of some further loss of optical energy, obscuration disks (for example, 222), apertures (for example, 224), as well as other spatial controlling devices such as annular ring apertures, can be arranged along the light propagation path to control the lighting uniformity of the ring light beam and illumination on the target (retina). These disks and apertures are also used to block the light beam from entering an undesired area, and to control the divergence/convergence angle of the light beam from the ring shaped light. Other optical elements such as polarizers and beam splitters can also be included in the optical imaging and relay system 212 for other purposes.

It should be understood that one aspect of the presently described embodiment is homogenizing a beam of light and transforming it into a ring beam with substantially improved angular flux distribution. This example which combines a light homogenizer with a solid cone shaped optical device has been described. However, the same light beam transformation can also be achieved by other means. For example, the light homogenizer can be replaced by other light homogenization elements such as a simple optical diffuser, although such a diffuser may not be as efficient as a light homogenizer. The light pipe can have different cross sectional shapes, including a square shape and the shape of polygon of an even number of sides. It can also be made with a multiple number of combined polygon shaped small light pipe arrays. The axicon can be made from any optically transparent material such as glass and plastic.

Figure 3:
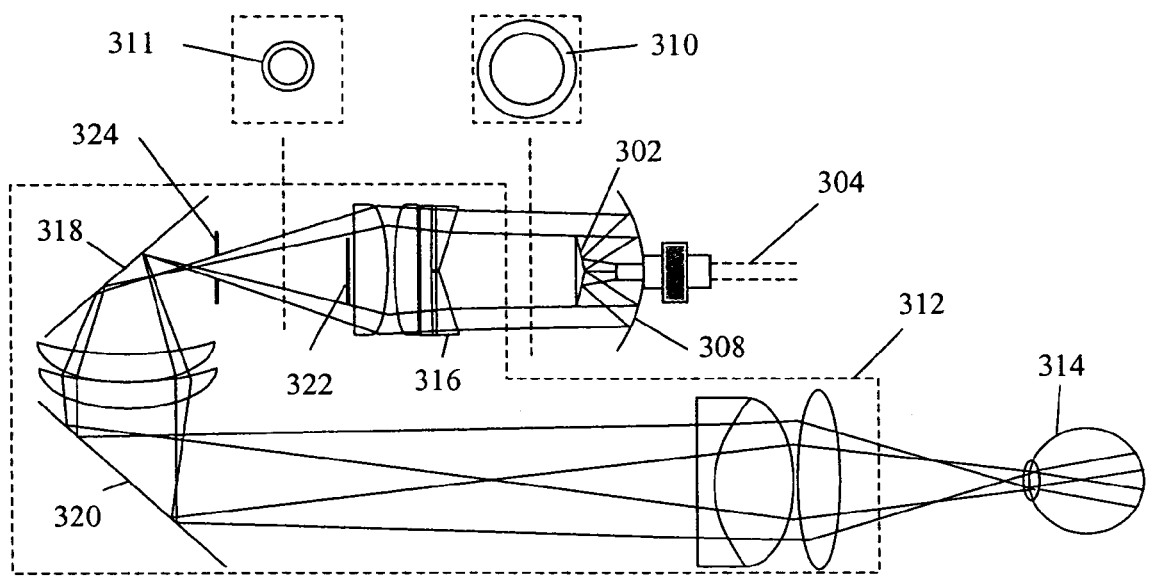
FIG. 3 shows an example of the use of a convex conical surface mirror as the ring beam transformer.
Figure 4:
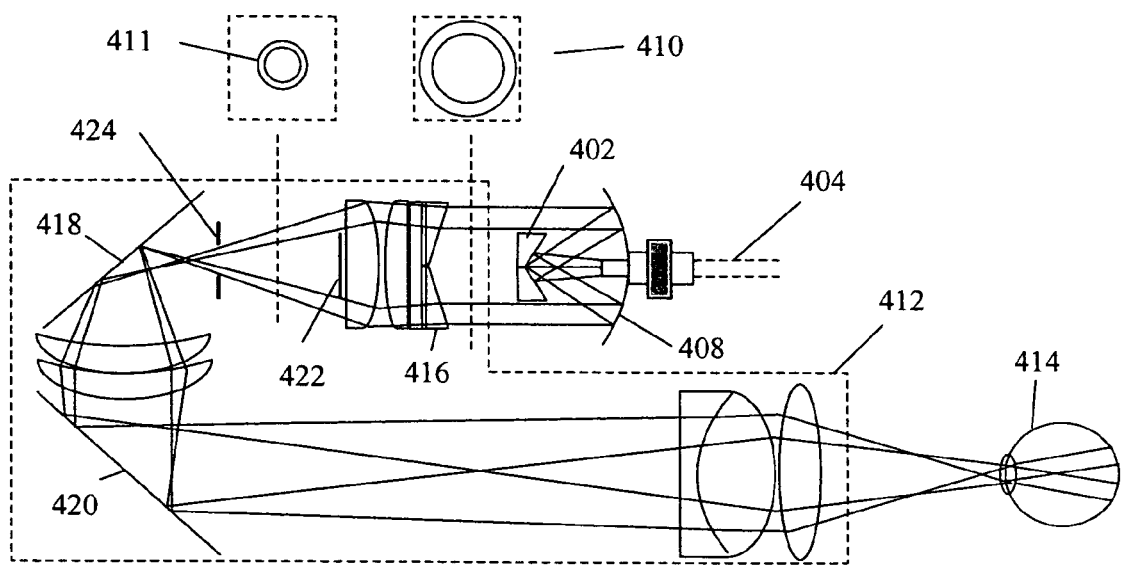
FIG. 4 shows an example of the use of a concave conical surface mirror as the ring beam transformer.

The ring beam transformer can also be constructed by using an annular ring spatial filter in the place of the axicon. Thus the term "ring beam transformer" should be interpreted in terms of its function. As shown in FIG. 3, the optical device 302 can be a transparent solid cone, but it can also be designed in a reflective configuration. A convex conical surface mirror 302 can be placed at a certain distance from the output end of the fiber bundle and the radially outwardly deflected beam can be further collimated by the parabaloidal mirror 308 as has been described with reference to FIG. 2. Note that a concave reflective conical surface mirror 402 can also be used as shown in FIG. 4, and in such a case the distance between the mirror and the output end of the fiber bundle needs to the adjusted accordingly so that the divergent ring beam still appears to come substantially from a linear light source near the focal point of the parabaloidal reflector.

In the configuration with remote light source and use of fiber optic bundle, the light homogenizer can also be arranged at the output side of the fiber optic bundle before the light beam goes through the shape transforming process, or at both sides of the fiber optic bundle. Furthermore, the filter wheel can also be arranged in front of the light pipe instead of being between the light pipe and the fiber optic bundle. In this configuration, the pair of lenses (114 and 120) can be removed and the light pipe homogenizer and fiber optic bundle can be directly bonded together, although this may slightly affect the spectral filtering of light as more light rays will now pass through the filters at more non-normal angles. Note that the filter wheel can also be arranged at the output side of the fiber optic bundle or after the beam has been transformed to a ring shape. In fact, the filter wheel can be arranged anywhere along the light path.

Figure 5:
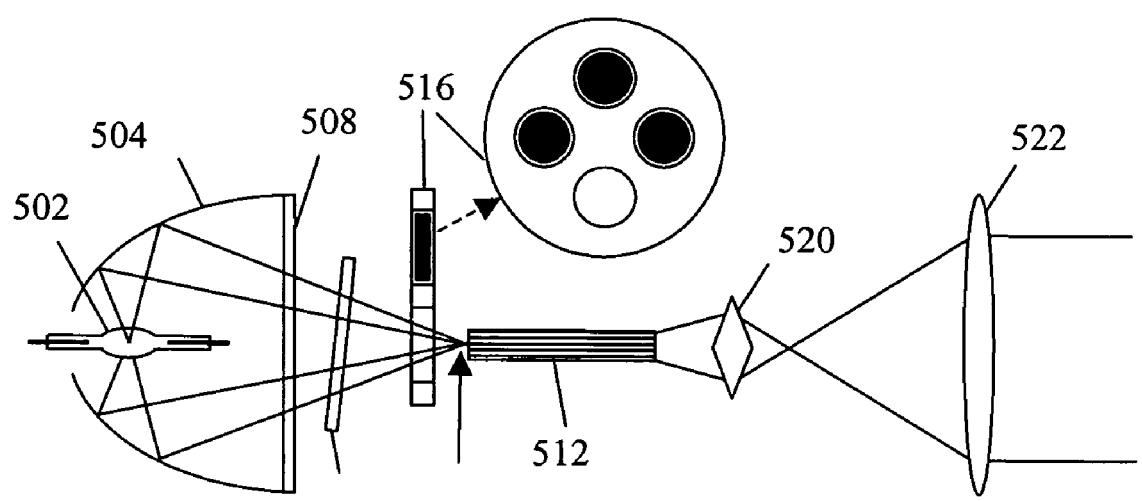
FIG. 5 shows an example of the use of an Axicon lens as the ring beam transformer.

A basic principle of the ring beam generating mechanism described in these embodiments can also be applied in cases where the light source is not located remotely. As shown in FIG. 5, the ring beam transformer can also be implemented as an Axicon lens 520 and condensing lens 522, in which the radially deflected beam from 520 can be further collimated by an additional lens 522 to form a ring light beam. The collimated ring beam can be further propagated using a similar optical beam manipulation and relay system as described with reference to FIG. 2. Note that in FIG. 5 a system configuration variation is depicted in which the filter wheel is arranged in front of the light homogenizer, although in such a case the light rays passing through the filter(s) will no longer be as collimated as in the FIG. 1 case. The Axicon lens 520 shown in FIG. 5 is bi-convex, however other types of Axicon lens can also be used, including bi-concave, plano-convex, plano-concave, and convex-concave ones, for the non-symmetric ones, the convex or concave side can be arranged either on the left or the right side.

Figure 6:
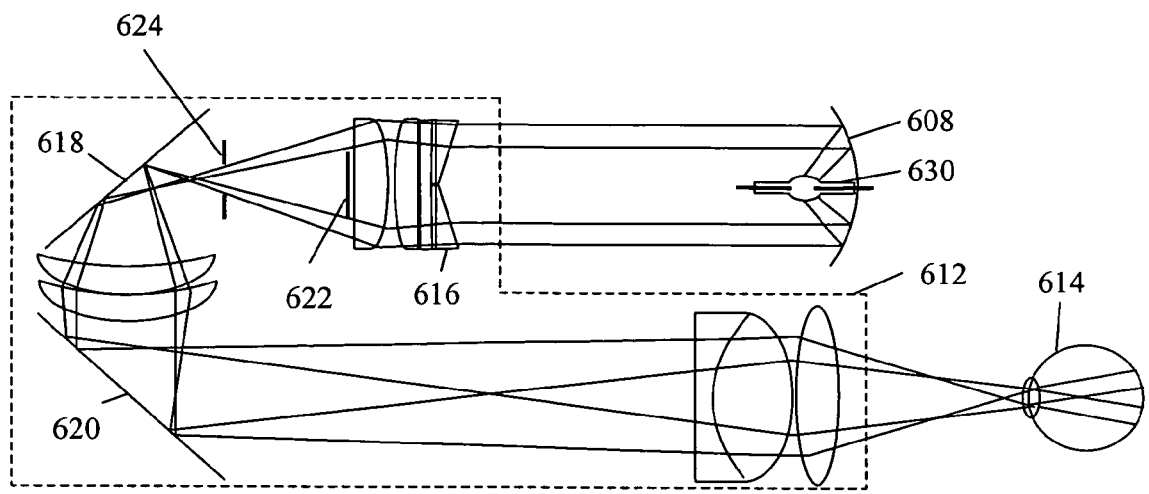
FIG. 6 shows an example of a compact version of an optical configuration that can collect and deliver a ring beam from a substantially linear light source to a sample for imaging application.

As another embodiment, FIG. 6 shows a more compact configuration where the Arc lamp 630 is directly integrated into the optical path to generate a collimated beam, which is then injected into the beam manipulation and relay system 612. In such a case, the arc lamp 630 can be coaxially placed with its linear discharge source substantially at the focus point of the parabaloidal reflector 608. Using this simple configuration, the issue associated with the blocking of emitted light by the electrodes of the arc lamp is no longer a concern, as the ring beam, which will be collected by the parabaloidal reflector and spatially filtered by the following optical beam manipulation and relay system, will not come from the axially low angular central solid cone portion of the light source.

Figure 7:
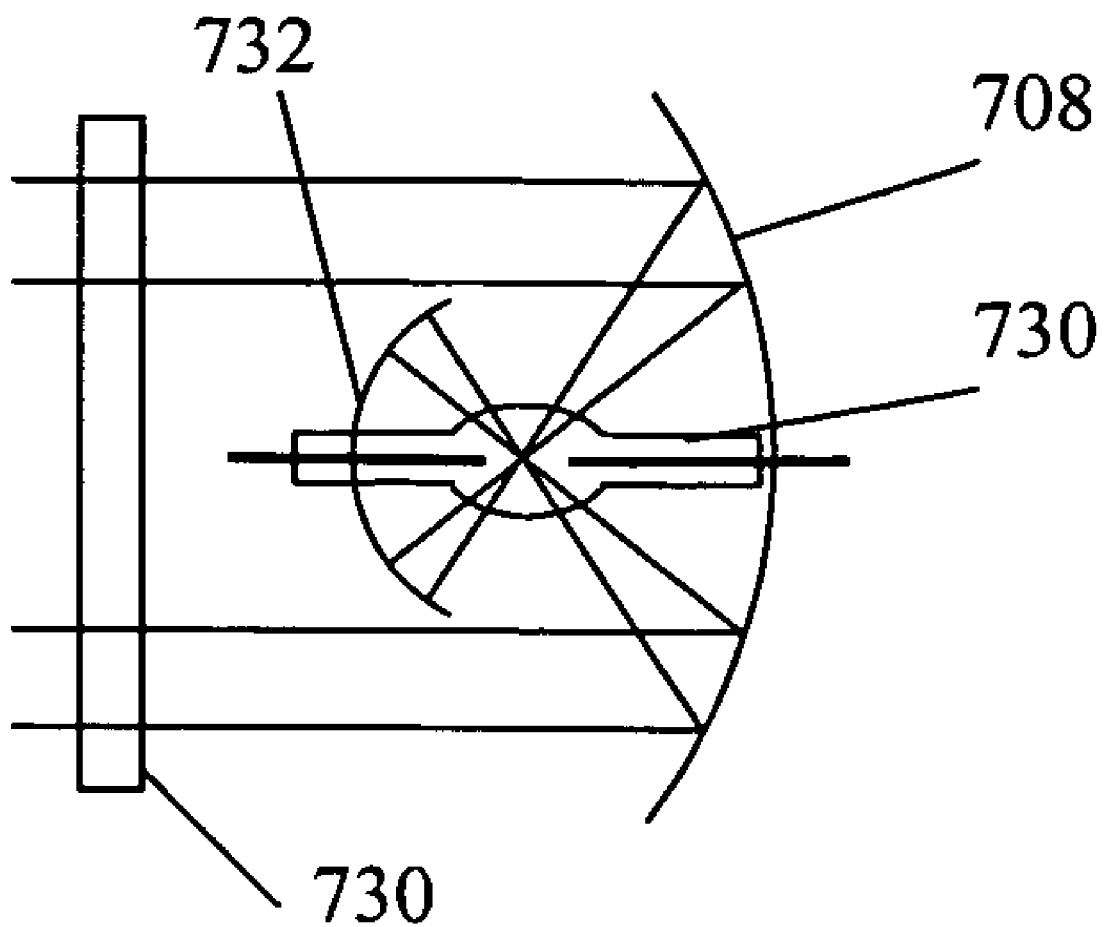
FIG. 7 shows an example of one enhanced embodiment of FIG. 6, in which a small spherical mirror is used to nearly double the amount of light collected and a homogenizer is inserted in the ring beam path to adjust the numerical aperture.

It is clear from FIG. 6 that only a small portion of the light emitted from the arc lamp is collected for generating ring beam due to the small collection angle range. The light collection efficiency can be further improved by placing other optical element(s) such as a reflector on the opposite side of the arc source so that the light emitted from that direction is bounced back and refocused at the light emitting plasma. The total light flux measured from the ring beam could be increased. Meanwhile, optical filters can also be inserted in the optical path to remove the hazardous radiation. FIG. 7 shows one example of such a configuration in which a small spherical mirror 732 is arranged on the other side with the arc lamp source 730 located at the center of the spherical mirror so that an almost equal amount of light as initially collected will be reflected back to the arc lamp source and then collected by the parabaloidal reflector. In addition, an optical filter 734 can be inserted in the nearly collimated ring beam to help remove hazardous radiation or select the desired spectrum of useful light.

In regard to other parts of the overall optical configuration, there exist a number of variations. For example, the ellipsoidal mirror 504 in FIG. 5 used for collecting the arc lamp light can be replaced by other types of mirrors or lenses such as a single lens or a combination of lenses or a combination of lens(es) and mirror(s). In addition, the use of the fiber bundle is not a must as the solid cone 202, or the convex conical surface mirror 302, or the concave conical surface mirror 402, or the Axicon lens 520 can also be directly arranged on the output side of a homogenizer to directly transform the homogenized beam into a ring beam.

Note that the presently disclosed optical arrangement does not need to be restricted to application in eye imaging. It can be used for any optical system that requires a ring illumination beam with a homogenized angular flux distribution. With the present arrangement, the central axial part of the optical beam path can be used for capturing the object reflected and/or scattered light to produce a good image of the object and as a result, the illumination optical path and the imaging optical path can be well separated and hence not interfering with each other. In additional to medical imaging devices such as ophthalmoscopes, microscopes and endoscopes, the present configuration can also be used in other applications such as machine vision.

The invention has now been described with reference to the preferred embodiments. Alternatives and substitutions will now be apparent to persons of skill in the art. Accordingly, it is not intended to limit the invention except as provided by the appended claims.

What is claimed is:

1. A system comprising:
  a parabaloidal mirror having a focal point on an axis of symmetry;
  an optical transformation element optically coupled to the input end of a fiber optic light conductor and positioned at about the equivalent focal point of the parabaloidal mirror, with the optical transformation element adapted to convert a disk image of an input end of a coupled fiber optic light conductor to a linear image substantially aligned along the axis of symmetry;
  a mirror positioned along the axis of symmetry to reflect light output from the optical transformation element onto the parabaloidal mirror so that a ring-shaped beam is output when light is input from a coupled fiber optic light conductor.

2. The system of claim 1 further comprising:
  an optical relay system adapted to intercept light reflected from the parabaloidal mirror and deliver intercepted light in the form of a ring focused onto the pupil of a subject's eye so that the ring beam spreads out to illuminate a large area of the fundus of the eye.

3. The system of claim 2 where the optical relay system further comprises:
  an axicon lens having a refractive effect that changes the direction of the collimated beam radially in the fashion that the tilted beam is symmetric along an optical axis.

4. The system of claim 1 where the optical transformation element is a transparent solid cone.

5. The system of claim 1 where the optical transformation element and the mirror are a convex or concave conical surface mirror.

6. A system comprising:
  an ellipsoidal mirror having first and second focal points aligned along a first axis;
  an axially linear light source that generates an arc when energized, with the axially linear light source having a long axis on which first and second electrodes are aligned, with the axially linear light source positioned so that its long axis is substantially parallel to the first axis and with the arc generated by the axially linear light source positioned at about the location of the first focal point of the ellipsoidal mirror;
  a light homogenizing element having an input end and an output end, with the light homogenizing element positioned so that its input end is located at about the second focal point of the ellipsoidal mirror and adapted to collect light, output by the arc generated by the axially linear light source, that is reflected by the ellipsoidal mirror;
  an optical transformation element, optically coupled to the output end of the light homogenizing element and adapted to convert light collected from the light homogenizing element to a substantially linear image along an axis of symmetry;
  a reflective ring beam generator, aligned about the axis of symmetry, adapted to convert the light radiated from the linear image into a nearly collimated ring shaped light beam;
  a refractive element adapted to intercept the nearly collimated ring shaped light beam and change the direction of the nearly collimated ring shaped light beam radially to form a radially outward deflected ring shaped light beam; and
  an optical relay system adapted to intercept the radially outward deflected ring shaped light beam and to convert the radially outward deflected ring shaped light beam into a focused ring shaped light beam incident on the pupil of a subject's eye, where the focused ring shaped light beam spreads out to cover a large portion of the retina.

7. The system of claim 6 where the refractive element is an axicon lens.

8. The system of claim 6 where the optical transformation element is a fiber bundle that has a rod shaped input end and a fanned-out ring shaped output end.

9. The system of claim 6 where the ring beam transformer is a solid light guide that can transform an input beam to a ring shaped beam.

10. The system of claim 6 where the refractive element is a combination of optical elements that can change the light ray propagation direction in a radially outward or inward manner.

11. A system comprising:
  an axially linear light source that generates an arc when energized, with the axially linear light source having a long axis on which first and second electrodes are aligned, with the axially linear light source positioned so that its long axis is substantially parallel to a first axis;

a parabaloidal mirror having a focal point aligned along the first axis and with the are generated by the axially linear light source positioned at about the location of the focal point where the parabaloidal mirror reflects light into a nearly collimated light beam;

a refractive element adapted to intercept the nearly collimated light beam and change the direction of the nearly collimated light beam radially to form a radially outward deflected light beam; and an optical relay system adapted to intercept the radially outward deflected ring shaped light beam and to convert the outwardly deflected ring shaped light beam into a focused ring shaped light beam incident on the pupil of a subject's eye, where the focused ring shaped light beam spreads out to cover a large portion of the retina.

12. The system of claim 11 where the refractive element comprises:

an axicon lens having a refractive effect that changes the direction of the collimated beam radially in the fashion that the tilted beam is symmetric along an optical axis.

13. A method for collecting light from a linear light source and transforming the collected light into a ring beam, the method comprising:

collecting light output from the linear light source;

homogenizing collected light to increase spatial and angular distribution uniformity of the radiation flux of the collected light;

transforming homogenized light into a nearly collimated ring shaped light beam;

changing the direction of the nearly collimated ring shaped light beam radially to form a radially outward deflected ring shaped light beam;

converting the radially outward deflected ring shaped light beam into a focused ring shaped light beam incident on the pupil of a subject's eye, where the focused ring shaped light beam spreads out to cover a large portion of the retina.

14. The method of claim 13 further comprising:

focusing homogenized light onto the input end of a fiber optic light conductor;

and where transforming homogenized light into a nearly collimated ring beam comprises:

converting an image of a disk shaped input end into an image of a linear light source positioned at about the focal point of a parabaloidal mirror 15. A system comprising:

means for collecting light output from a linear light source;

means for homogenizing collected light to increase spatial and angular distribution uniformity of the radiation flux of the collected light;

means for transforming homogenized light into a nearly collimated ring beam;

means for changing the direction of the nearly collimated ring shaped beam radially to form a radially outward deflected ring shaped beam; and means for converting the outwardly deflected ring shaped light beam into a focused ring shaped light beam incident on the pupil of a subject's eye, where the focused ring shaped light beam spreads out to cover a large portion of the retina.

16. The system of claim 15 further comprising:

a fiber optic light conductor having a disk-shaped input end and an output end;

means for focusing homogenized light onto the input end of the fiber optic light conductor;

and where the means for transforming homogenized light into a collimated ring beam comprises;

means for converting an image of a disk shaped input end into an image of a linear light source positioned at about the focal point of a parabaloidal mirror.

* * * * *